United States Patent [19]

Lumma, Jr. et al.

[11] 4,081,542
[45] * Mar. 28, 1978

[54] PIPERAZINYLPYRAZINES

[75] Inventors: William C. Lumma, Jr., Lansdale; Walfred S. Saari, Pennsburg, both of Pa.

[73] Assignee: Merck & Co., Inc., Rahway, N.J.

[*] Notice: The portion of the term of this patent subsequent to Apr. 14, 1995, has been disclaimed.

[21] Appl. No.: 774,565

[22] Filed: Mar. 4, 1977

Related U.S. Application Data

[63] Continuation-in-part of Ser. No. 696,254, Jun. 15, 1976, abandoned, which is a continuation-in-part of Ser. No. 656,664, Feb. 9, 1976, abandoned, which is a continuation-in-part of Ser. No. 570,052, Apr. 21, 1975, abandoned.

[51] Int. Cl.² .................. C07D 295/12; A61K 31/495
[52] U.S. Cl. .................. 424/250; 260/268 H
[58] Field of Search .................. 424/250; 260/268 H

[56] References Cited

U.S. PATENT DOCUMENTS

| 2,543,972 | 3/1951 | Hultquist et al. | 260/268 |
| 2,562,036 | 11/1951 | Hultquist et al. | 260/268 |
| 2,606,906 | 10/1952 | Hultquist et al. | 260/268 |
| 3,331,843 | 7/1967 | Tomfucik et al. | 260/268 |

FOREIGN PATENT DOCUMENTS

| 1,369,379 | 10/1974 | United Kingdom | 260/268 |
| 1,407,552 | 9/1975 | United Kingdom | 260/268 |

OTHER PUBLICATIONS

Boissier et al., J. Med. Chem. 6 541 (1963).
Howard et al., J. Org. Chem. 18 1484 (1953).
Lutz et al., J. Org. Chem. 29 415 (1964).

*Primary Examiner*—Nicholas S. Rizzo
*Attorney, Agent, or Firm*—Rudolph J. Anderson, Jr.; Harry E. Westlake, Jr.; William H. Nicholson

[57] ABSTRACT

Compounds of the formula:

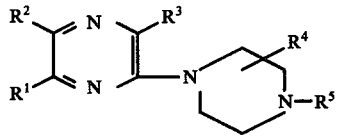

and their N-oxides and acid-addition salts are disclosed having pharmacological activity as anorexic agents.

4 Claims, No Drawings

PIPERAZINYLPYRAZINES

BACKGROUND OF THE INVENTION

This application is a continuation-in-part of copending application Ser. No. 696,254, filed June 15, 1976, now abandoned which in turn is a continuation-in-part of copending application Ser. No. 656,664, filed Feb. 9, 1976, (now abandoned), which in turn is a continuation-in-part of Ser. No. 570,052, filed Apr. 21, 1975 (now abandoned).

This invention relates to anorexic agents and to certain new compounds having anorexic activity, to a method of preparing these new compounds, to pharmaceutical formulations containing the anorexic compounds, and to methods of administering the anorexic agents to an animal or human.

Obesity is a fairly common condition and a potentially serious one in view of the correlation between incidence of various diseases and the degree to which a person is overweight. For example, obese persons succumb statistically more frequently to cardiovascular renal disease than do persons of normal weight. Obesity likewise results in higher death rates from diabetes, nephritis, pneumonia, cirrhosis, appendicitis and post-operative complications. Since obesity often occurs simply as a consequence of excessive intake of calories, good management of the condition in these cases can be achieved by restricting the caloric intake. Frequently, however, the patient has difficulty in initiating and maintaining dietary restrictions, making it necessary to employ anorexigenic drugs as adjuvants to therapy.

Accordingly, it is an object of the present invention to provide novel piperazinylpyrazines which are effective, anorexic agents. Another object is to provide pharmaceutical formulations for administration of these and other related anorexic agents. Further objects are to provide methods for preparing the novel piperazinylpyrazines and for administering piperazinylpyrazine anorexic agents to a mammalian animal or human.

DETAILED DESCRIPTION

The piperazinylpyrazine compounds useful in the novel method of treatment of the present invention have the structural formula:

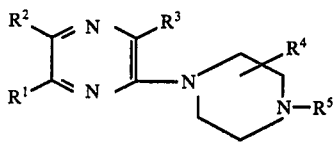

or N-oxide, or pharmaceutically acceptable salt thereof, wherein $R^1$ is hydrogen, halogen (F, Br or I), alkyl of from 1-4 carbon atoms, haloalkyl of from 1 to 3 carbon atoms, alkoxy of from 1 to 4 carbon atoms, amino, alkylthio of from 1 to 4 carbon atoms, phenylthio, carbamoyl or dialkylcarbamoyl wherein the alkyl groups are from 1 to 4 carbon atoms, carboalkoxy of from 1 to 5 carbon atoms, di(alkyl)amino of 2-6 carbon atoms, phenyl, or phenyl substituted by halogen (F, Cl, Br, or I), by alkyl of from 1 to 4 carbon atoms, or by alkoxy of from 1 to 3 carbon atoms;

$R^2$ is hydrogen, halogen (F, Cl, Br or I), alkyl of from 1 to 3 carbon atoms, cyano, amino, carboalkoxy of from 1 to 5 carbon atoms, carbamoyl, alkoxy of from 1 to 4 carbon atoms, haloalkyl of from 1 to 3 carbon atoms, phenyl or substituted phenyl wherein the substituent is halogen (F, Cl, Br or I);

$R^3$ is hydrogen, halogen (F, Cl, Br, or I), alkyl of from 1 to 3 carbon atoms, alkanoylamino of from 1 to 3 carbon atoms, carbamoyl, phenyl or phenyl substituted by halogen (F, Cl, Br or I), by alkyl of from 1 to 4 carbon atoms or by alkoxy from 1 to 3 carbon atoms;

$R^4$ is hydrogen, alkyl of from 1 to 3 carbon atoms, carboxyl or carboalkoxy of from 1 to 5 carbon atoms;

$R^5$ is hydrogen, or dialkylaminopropyl; wherein the alkyl groups are of 1-3 carbon atoms.

Preferably, $R^1$ and $R^2$ are as defined above and $R^3$ is hydrogen. Most preferably, $R^3$ is hydrogen and one of $R^1$ and $R^2$ is also hydrogen.

The novel compounds of the present invention have the structural formula:

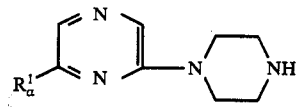

or N-oxide, or pharmaceutically acceptable salt thereof, wherein $R_a^1$ is
(1) lower alkoxy, especially $C_{1-4}$ alkoxy, such as methoxy,
(2) trifluoromethyl, or
(3) alkylthio of 1-3 carbon atoms.

The compounds useful in the novel method of treatment of the present invention of formula III are prepared by reaction of a 2-X-pyrazine of formula I with piperazine or a substituted piperazine of formula II (wherein $R^4$ and $R^5$ are as defined above).

The reaction sequence is as follows:

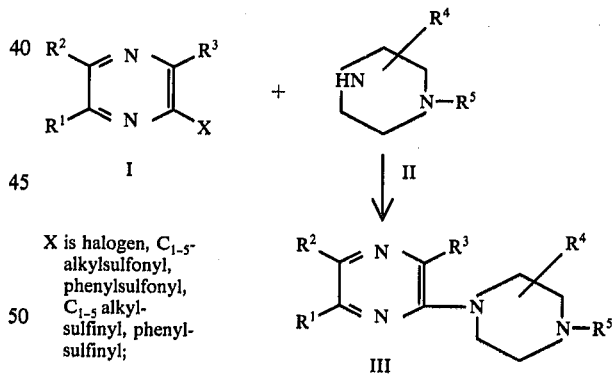

X is halogen, $C_{1-5}$-alkylsulfonyl, phenylsulfonyl, $C_{1-5}$ alkylsulfinyl, phenylsulfinyl;

The reaction takes place at temperatures ranging from about ambient to about 90° C., preferably under an inert atmosphere, e.g. $N_2$, He or Ar, until a substantial amount of desired adduct of formula III is obtained, typically for a period of from about 0.5 to about 6 hours, preferably from about 1 to about 4 hours.

The compounds active in the novel method of treatment of this invention may be administered as anorexic agents to mammalian species, e.g. rats and mice, in amounts ranging from about 0.01 to about 20 mg. per kg. of body weight, preferably from about 0.1 to about 10 mg. per kg. of body weight in a single dose or in 2 to 4 divided doses.

These compounds in the described dosages may be administered orally; however, other routes such as intraperitoneally, subcutaneously, intramuscularly, or intravenously may be employed.

The active compounds of the present invention are administered orally, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules, and the like, may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate, and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coating or to otherwise modify the physical form of the dosage unit, for instance, tablets, pills, or capsules may be coated with shellac, sugar, or both. A syrup or elixier may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

These pharmaceutical compositions form another embodiment of this invention and include the compounds previously described as active in the novel method of treatment except that $R^1$ and $R^3$ are not lower alkyl and with the proviso that $R^1$, $R^2$ and $R^3$ are not all hydrogen in the one compound.

As to the pharmaceutically acceptable salts, those coming within the purview of this invention include the pharmaceutically acceptable acid-addition salts. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicylic, succinic acid, theophylline, 8-chlorotheophylline, p-aminobenzoic, p-acetamidobenzoic, or methanesulfonic.

In addition to the anorexic activity described above, the novel compounds of this invention pharmacologically influence serotonin levels in a manner that suggests they are useful as antidepressant, antihypertensive, analgesic and sleep inducing agents. For these purposes, the same routes of administration, and pharmaceutical formulations as described above would be employed.

The following examples illustrate the present invention without, however, limiting the same thereto. Unless otherwise indicated, all temperatures are expressed in degrees Celsius.

EXAMPLE 1

6-Chloro-2(1'-piperazinyl)pyrazine hydrochloride 2,6-Dichloropyrazine (0.10 mole) is added to 20 g. piperazine in 200 ml. acetonitrile and the mixture refluxed 1.5 hr. under $N_2$. The mixture is concentrated in vacuo and the residue partitioned between 1N aqueous NaOH and benzene. The combined benzene extracts are washed with 1N aqueous NaOH, dried over $MgSO_4$, filtered and concentrated in vacuo to a yellow oil which is dissolved in 200 ml. absolute ethanol containing 10 ml. of cold, saturated anhydrous ethanolic HCl. The precipitated hydrochloride is recrystallized from 95% ethanol to give faintly yellow needles, m.p. 350° dec.

EXAMPLE 2

5-Chloro-2-(1'-piperazinyl)-pyrazine hydrochloride

The title compound, m.p. 301°–302°, is prepared similarly to Example 1 by substituting 2,5-dichloropyrazine for 2,6-dichloropyrazine.

EXAMPLE 3

6-(Phenylthio)-2-(1-piperazinyl)pyrazine hydrochloride

Step A: Preparation of 6-phenylthio-2-chloropyrazine

A mixture of 2,6-dichloropyrazine (0.100 mol) and freshly distilled thiophenol (0.100 mol) in 200 ml. N,N-dimethylformamide is treated with five grams of sodium hydride (50% dispersion in Nujol) gradually with vigorous stirring under nitrogen at room temperature. After 3 hr. the mixture is concentrated in vacuo, and the residue partitioned between water and benzene. The benzene extract is washed with water, dried (anhydrous sodium sulfate), and concentrated in vacuo to an oil which is the crude title compound.

Step B: Preparation of 6-(phenylthio)-2-(1-piperazinyl)-pyrazine hydrochloride

The crude intermediate is combined with excess piperazine (40 grams) in 250 ml. of acetonitrile and the mixture refluxed 2 hr. under $N_2$. The solvent is removed in vacuo, and the residue partitioned between 2N aqueous sodium hydroxide and chloroform. The combined chloroform extracts are extracted with 1.2 N aqueous hydrochloric acid. The acid extracts are basified to pH 10 with sodium hydroxide and the crude product extracted with chloroform. The combined chloroform extracts were washed with two volumes of 2N sodium hydroxide, dried (anhyd. sodium sulfate) and concentrated in vacuo to the crude base which is converted to the hydrochloride in ethanolic hydrogen chloride. The hydrochloride salt is recrystallized from absolute ethanol to give the title compound, m.p. 221°–222°.

EXAMPLE 4

6-Trifluoromethyl-2-(1'-piperazinyl)-pyrazine hydrochloride

2-Pyrazinoic acid (25 g., 0.20 mole) is converted to 2-trifluoromethylpyrazine by heating with sulfur tetrafluoride (54 g.) at an initial pressure of 160 psi and 150° in a stainless steel autoclave for 6 hours. After quenching the reaction mixture on ice and adding sufficient NaOH to adjust the pH to 6, the crude product is extracted into methylene chloride. Distillation gives 2-trifluoromethylpyrazine, b.p. 118°. The freshly distilled 2-trifluoromethylpyrazine (15.9 g.) is converted to the 4-N-oxide with 30 ml. glacial acetic acid and 20 ml. 30% aqueous hydrogen peroxide for 48 hours at 70°. After quenching the reaction mixture on ice, the product is extracted into benzene. The benzene extracts are washed with aqueous sodium carbonate, dried ($Na_2SO_4$) and concentrated in vacuo to give the crystalline 4-N-oxide, m.p. 57°–59°. The N-oxide (3.28 g.) is rearranged nearly exclusively to 2-chloro-6-trifluoromethylpyrazine, b.p. 115° (25 in. Hg) by heating with 5 ml. benzenesulfonylchloride for 4 hours at 100° and distilling the reaction mixture.

The title compound, m.p. 292°–294°, is prepared similarly to Example 1, starting from the 2-chloro-6-trifluoromethylpyrazine prepared as described above.

EXAMPLE 5

6-Methoxy-2-(1'-piperazinyl)-pyrazine dihydrochloride 2,6-Dichloropyrazine (0.067 mole) is treated with a solution of sodium methoxide (0.067 mole) in 100 ml. dry methanol for 1 hour at 25°. The solvent is removed in vacuo and the residue is extracted with boiling hexane extract. 2-Chloro-6-methoxypyrazine crystallizes from the hexane extract. Another recrystallization from isopropanol at −70° gives 2-chloro-6-methoxypyrazine as an oil at room temperature.

The title compound, m.p. 189°–191°, is prepared similarly to Example 1, using the 2-chloro-6-methoxypyrazine prepared as described above in place of 2,6-dichloropyrazine.

EXAMPLE 6

6-Chloro-2-(1'-piperazinyl)-pyrazine-1-oxide

2-Chloropyrazine (0.1 mole) is added to a solution of 0.3 mole trifluoroperacetic acid in $CH_2Cl_2$ (300 ml.) at 0°. The mixture is stirred 4 hours at 0°, 4 hours at 25° and finally at reflux for 4 hours. The resulting solution is washed with saturated aqueous NaCl solution and then saturated aqueous $Na_2CO_3$ solution and concentrated in vacuo to give crude 2-chloropyrazine-1,4-dioxide.

The crude 2-chloropyrazine-1,4-dioxide, 20 g., is stirred 4 hours with 50 ml. benzenesulfonyl chloride at 50° under $N_2$ and quenched on a mixture of ice, pyridine and saturated NaCl solution. The precipitated 2,6-dichloropyrazine-1-oxide is collected by filtration and converted to the title compound by reaction with piperazine as in Example 1.

EXAMPLE 7

6-Chloro-2-(1'-piperazinyl)-pyrazine-4-oxide

Similarly to Example 6, 2,6-dichloropyrazine is converted to the 4-oxide with 1.8 molar equivalents of trifluoroperacetic acid. The crude 2,6-dichloropyrazine-4-oxide is converted to the title compound by reaction with piperazine as in Example 1.

EXAMPLES 8–23

Following the procedure of Example 1, the following substituted halopyrazines are reacted with piperazine in acetonitrile to give the corresponding 2-(1'-piperazinyl)-pyrazine derivatives.

| Example | Starting Material | Product |
|---|---|---|
| 8 | 2,3-Dibromopyrazine | 3-Bromo-2-(1'-piperazinyl)-pyrazine hydrochloride |
| 9 | 2,6-Dibromopyrazine | 6-Bromo-2-(1'-piperazinyl)-pyrazine hydrochloride |
| 10 | 2-Chloro-3,5-diphenylpyrazine | 3,5-Diphenyl-2-(1'-piperazinyl)-pyrazine hydrochloride |
| 11 | 2-Chloro-3,6-diphenylpyrazine | 3,6-Diphenyl-2-(1'-piperazinyl)-pyrazine hydrochloride |
| 12 | 2-Chloro-5,6-diphenylpyrazine | 5,6-Diphenyl-2-(1'-piperazinyl)-pyrazine hydrochloride |
| 13 | 6-Benzylthio-2-chloropyrazine | 6-Benzylthio-2-(1'-piperazinyl)-pyrazine hydrochloride |
| 14 | 6-Carbamoyl-2-chloropyrazine | 6-Carbamoyl-2-(1-piperazinyl)-pyrazine hydrochloride |
| 15 | 2-Chloro-6-diethylcarbamoylpyrazine | 6-Diethylcarbamoyl-2-(1'-piperazinyl)-pyrazine hydrochloride |
| 16 | 6-Carbomethoxy-2-chloropyrazine | 6-Carbomethoxy-2-(1'-piperazinyl)-pyrazine hydrochloride |
| 17 | 5-Carbamoyl-2-chloropyrazine | 5-Carbamoyl-2-(1'-piperazinyl)-pyrazine hydrochloride |
| 18 | 2-Chloro-5-methoxypyrazine | 5-Methoxy-2-(1'-piperazinyl)-pyrazine hydrochloride |
| 19 | 2-Chloro-5-trichloromethylpyrazine | 5-Trichloromethyl-2-(1'-piperazinyl)-pyrazine hydrochloride |
| 20 | 2-Chloro-5-phenylpyrazine | 5-Phenyl-2-(1'-piperazinyl)-pyrazine hydrochloride |
| 21 | 2-Chloro-5-cyanopyrazine | 5-Cyano-2-(1'-piperazinyl)-pyrazine hydrochloride |
| 22 | 2-Chloro-5-(p-chlorophenyl)-pyrazine | 5-(p-chlorophenyl)-2-(1'-piperazinyl)-pyrazine hydrochloride |
| 23 | 5-Amino-2-chloropyrazine | 5-Amino-2-(1'-piperazinyl)-pyrazine hydrochloride |

EXAMPLE 24

6-(N,N-dimethylamino)-2-(1-piperazinyl)pyrazine dihydrochloride

Twenty millimoles (3.14 g.) of 6-(N,N-dimethylamino)-2-chloropyrazine and piperazine (3 g.) are fused under $N_2$ at 135° for 6 hours. The mixture is digested with water and after filtering to remove insolubles, is basified with 10 N sodium hydroxide and extracted with chloroform. The combined chloroform extracts are washed with 2 N sodium hydroxide, dried (sodium sulfate, anhyd.), filtered, and concentrated to an oil under reduced pressure. The product is isolated as the dihydrochloride salt, m.p. 249°–250°, from isopropanol.

EXAMPLES 25–34

The 2-hydroxypyrazine derivatives (0.10 mole) listed below are converted to the corresponding substituted 2-chloropyrazine by reaction with 0.40 mole phosphorus oxychloride and 10 ml. N,N-dimethylformamide at reflux for 1–4 hours. After quenching the reaction mixture on ice, the substituted 2-chloropyrazine is isolated by extraction into ethyl ether or benzene or by crystallization of the separated product. The 2-chloropyrazine derivatives in turn are converted to the corresponding 2-(1'-piperazinyl)-pyrazine derivatives by reaction with piperazine following the procedure of Example 1.

| Example | Starting Material | Product |
|---|---|---|
| 25 | 3,6-Di-(4-bromophenyl)-pyrazin-2-ol | 3,6-Di-(4-bromophenyl)-2-(1'-piperazinyl)-pyrazine hydrochloride |

-continued

| Example | Starting Material | Product |
|---|---|---|
| 26 | 3,6-Di-(4-butyl-phenyl)-pyrazin-2-ol | 3,6-Di-(4-butylphenyl)-2-(1'-piperazinyl)-pyrazine hydrochloride |
| 27 | 3,6-Di-(4-methoxy-phenyl)-pyrazin-2-ol | 3,6-Di-(4-methoxyphenyl)-2-(1'-piperazinyl)-pyrazine hydrochloride |
| 28 | 3-Acetamidopyrazin-2-ol | 3-Acetamido-2-(1'-piperazinyl)-pyrazine hydrochloride |
| 29 | 3-Hydroxypyrazin-2-carboxamide. erazinyl)-pyrazine | 3-Carbamoyl-2-(1'-piperazinyl)-pyrazine hydrochloride |
| 30 | 3-Hydroxy-5-methyl-pyrazin-2-carboxamide | 3-Carbamoyl-5-methyl-2-(1'-piperazinyl)-pyrazine hydrochloride |
| 31 | 5,6-Dimethyl-3-hydroxypyrazin-2-carboxamide | 3-Carbamoyl-5,6-dimethyl-2-(1'-piperazinyl)-pyrazine hydrochloride |
| 32 | 5,6-Diphenyl-3-hydroxypyrazin-2-carboxamide | 3-Carbamoyl-5,6-diphenyl-2-(1'-piperazinyl)-pyrazine hydrochloride |
| 33 | 3-Methyl-5-phenyl-pyrazin-2-ol | 3-Methyl-5-phenyl-2-(1'-piperazinyl)-pyrazine hydrochloride |
| 34 | 5,6-Dimethyl-3-phenylpyrazin-2-ol | 5,6-Dimethyl-3-phenyl-2-(1'-piperazinyl)-pyrazine hydrochloride |

EXAMPLE 35

2-(3'-Carbethoxy-1'-piperazinyl)-pyrazine hydrochloride

The title compound is prepared similarly to Example 1 by substituting 2-chloropyrazine for 2,6-dichloropyrazine and 2-carbethoxypiperazine for piperazine.

EXAMPLE 36

2-(3'-Carboxy-1'-piperazinyl)-pyrazine hydrochloride

A solution of 5 g. of 2-(3'-carbethoxy-1'-piperazinyl)-pyrazine hydrochloride in 50 ml. of 1 N hydrochloric acid is stirred at reflux for two hours. After concentrating under reduced pressure at 50° absolute ethanol is added to the residue and the solution reconcentrated. The addition of ethanol and concentration is repeated two more times. The residue is recrystallized from a methanol ethyl acetate mixture to give 2-(3'-carboxy-1'-piperazinyl)-pyrazine hydrochloride.

EXAMPLE 37

6-Methylthio-2-(1'-piperazinyl)-pyrazine hydrochloride

A mixture of 0.13 mole of sodium methylmercaptide (prepared from 3.12 g. sodium hydride and excess methyl mercaptan), 20 g. (0.13 mole) of 2,6-dichloropyrazine and 200 ml. benzene is heated at reflux for 24 hours, cooled and washed twice with 50 ml. water. The benzene layer is separated, dried over anhydrous sodium sulfate, filtered and concentrated under reduced pressure. Distillation of the residue gives 2-chloro-6-methylthiopyrazine.

To a solution of 10 g. piperazine in 150 ml. of 2-butanol is added 8.03 g. (0.050 mole) of 2-chloro-6-methylthiopyrazine. After heating at reflux under nitrogen for 6 hours, solvent is removed under reduced pressure and the residue partitioned between dilute sodium hydroxide solution and benzene. The benzene extract is washed with water, dried over anhydrous magnesium sulfate, filtered and concentrated under reduced pressure. The residue is dissolved in ethanol and acidified with anhydrous ethanolichydrogen chloride solution. The precipitated salt is recrystallized from a methanol-ethyl acetate mixture to give 6-methylthio-2-(1'-piperazinyl)-pyrazine hydrochloride.

EXAMPLE 38

Preparation of Capsule Formulation

| Ingredient | Milligrams per Tablet |
|---|---|
| 6-trifluoromethyl-2-(1'-piperazinyl)pyrazine hydrochloride | 6 |
| Starch | 87 |
| Magnesium stearate | 7 |

The active ingredient, starch and magnesium stearate are blended together. The mixture is used to fill hard shell capsules of a suitable size at a fill weight of 100 milligrams per capsule.

EXAMPLE 39

Preparation of Tablet Formulation

| Ingredient | Milligrams per Tablet |
|---|---|
| 6-methoxy-2-(1'-piperazinyl)-pyrazine hydrochloride | 12 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 12 milligrams of active ingredient.

EXAMPLE 40

Preparation of Oral Syrup Formulation

| Ingredient | Amount | |
|---|---|---|
| 6-methylthio-2-(1'-piperazinyl)-pyrazine hydrochloride | 25 | mg. |
| Sorbitol solution (70% N.F.) | 40 | ml. |
| Sodium benzoate | 150 | mg. |
| Sucaryl | 90 | mg. |
| Saccharin | 10 | mg. |
| Cherry Flavor | 50 | mg. |
| Distilled water qs to | 100 | ml. |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

EXAMPLE 41

On the day immediately preceding the test day (control day) the food consumption is measured for groups of from 7 to 10 rats allowed access to food for only 2 hours per day. On the next day (test day) the rats are injected i.p. with different dose levels of the test compound 3 minutes prior to commencement of the 2-hour feeding period. Food consumption on the test day is then measured and compared (paired t-test) with consumption on the control day. The results using representative compounds of the present invention are set forth in the following table.

| Compound of Example | Dose mg/ kg i.p. | Grams Eaten on Control Day | Grams Eaten on Test Day |
|---|---|---|---|
| 2 | 6.0 | 15.9 ± 2.9 | 5.5 ± 2.2 |
| 4 | 3.0 | 14.0 ± 2.3 | 8.3 ± 2.1 |
| 5 | 6.0 | 12.3 ± 4.6 | 3.1 ± 0.9 |

*Standard Deviation.

What is claimed is:

1. A compound of the formula:

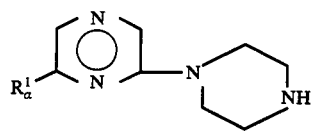

or an N-oxide
or pharmaceutically acceptable salt thereof, wherein
$R_a^1$ is trifluoromethyl, alkoxy of from 1-4 carbon atoms, or, alkylthio of 1-4 carbon atoms.

2. A method of decreasing food intake in a mammalian species which comprises administering to a host animal an effective amount of a compound of formula:

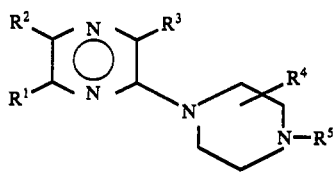

or an N-oxide or a pharmaceutically acceptable salt thereof, wherein
$R^1$ is hydrogen, bromo, alkyl of from 1-4 carbon atoms, haloalkyl of from 1-3 carbon atoms, alkoxy of from 1-4 carbon atoms, amino, alkylthio of from 1-4 carbon atoms, phenylthio, carbamoyl or dialkylcarbamoyl wherein alkyl groups are from 1-4 carbon atoms, carboalkoxy of from 1-5 carbon atoms, di(alkyl)amino of 2-6 carbon atoms, phenyl or phenyl substituted by halogen, by alkyl of from 1-4 carbon atoms or by alkoxy of from 1-3 carbon atoms;

$R^2$ is hydrogen, halogen, alkyl of from 1-3 carbon atoms, cyano, amino, carboalkoxy of from 1-5 carbon atoms, carbamoyl, alkoxy of from 1-4 carbon atoms, haloalkyl of from 1-3 carbon atoms, phenyl, or phenyl substituted by halogen;

$R^3$ is hydrogen, halogen, alkyl of from 1-3 carbon atoms, alkanoylamino of from 1-3 carbon atoms, carbamoyl, phenyl or phenyl substituted by halogen, by alkyl of from 1-4 carbon atoms, or by alkoxy of from 1-3 carbon atoms;

$R^4$ is hydrogen, alkyl of from 1-3 carbon atoms, carboxyl or carboalkoxy; and $R^5$ is hydrogen, dialkylaminopropyl, wherein the alkyl groups are of 1-3 carbon atoms.

3. The method of claim 2 wherein the compound is

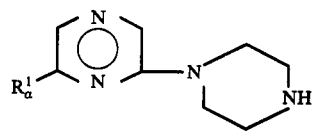

or N-oxide or pharmaceutically acceptable salt thereof, wherein
$R_a^1$ is trifluoromethyl, alkoxy of from b 1-4 carbon atoms, or, alkylthio, of 1-4 carbon atoms.

4. The pharmaceutical composition for decreasing food intake in a mammalian species comprising a pharmaceutical carrier and an effective amount of a compound of formula:

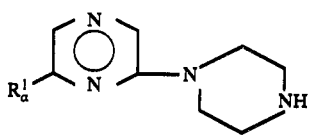

or N-oxide or pharmaceutically acceptable salt thereof, wherein
$R_a^1$ is trifluoromethyl, alkoxy of from 1-4 carbon atoms, alkylthio of 1-4 carbon atoms.

* * * * *